United States Patent [19]
Albagli et al.

[11] Patent Number: 5,616,464
[45] Date of Patent: Apr. 1, 1997

[54] NUCLEIC ACID SEQUENCE DETECTION EMPLOYING AMPLIFICATION PROBES

[75] Inventors: David Albagli, Palo Alto; Reuel VanAtta, Mountain View; Michael Wood, Palo Alto, all of Calif.

[73] Assignee: NAXCOR, Menlo Park, Calif.

[21] Appl. No.: 364,339

[22] Filed: Dec. 27, 1994

[51] Int. Cl.$^6$ .............. C12Q 1/68; C12P 19/34; C07H 21/04; C12N 15/00
[52] U.S. Cl. ........... 435/6; 435/91.1; 435/91.2; 536/23.1; 536/24.3; 536/24.32; 935/8; 935/76; 935/77; 436/2; 436/94; 436/805; 436/905
[58] Field of Search .............. 435/6, 91.1, 91.2, 435/270; 536/23.1, 24.3–24.32; 935/76, 77, 8; 436/2, 805, 905, 94

[56] References Cited

U.S. PATENT DOCUMENTS

| | | | |
|---|---|---|---|
| 4,820,630 | 4/1989 | Taub | 435/5 |
| 4,851,330 | 7/1989 | Kohne | 435/6 |
| 4,883,750 | 11/1989 | Whiteley et al. | 435/6 |
| 5,139,940 | 8/1992 | Isaacs et al. | 435/91 |
| 5,424,413 | 6/1995 | Hogan et al. | 536/24.31 |
| 5,449,602 | 9/1995 | Royer et al. | 435/6 |

FOREIGN PATENT DOCUMENTS

| | | |
|---|---|---|
| 0097373B1 | 1/1984 | European Pat. Off. . |
| 0320308B1 | 6/1989 | European Pat. Off. . |
| 0336731B1 | 5/1994 | European Pat. Off. . |
| 0324616B1 | 3/1995 | European Pat. Off. . |
| 94/29485 | 12/1994 | WIPO .............. C12Q 1/68 |

OTHER PUBLICATIONS

Guatelli, et al., Isothermal, In Vitro Amplification of Nucleic Acids by a Multienzyme Reaction Modeled after Retroviral Replication (Mar. 1990) Proc. Natl. Acad. Sci., vol. 87:1874–1878.

Barany, Genetic Disease Detection and DNA Amplification Using Cloned Thermostable Ligase (Jan. 1991) Proc. Natl. Acad. Sci., vol. 88:189–193.

*Primary Examiner*—Bradley L. Sisson
*Attorney, Agent, or Firm*—Flehr, Hohbach, Test, Albritton & Herbert; Bertram I. Rowland

[57] ABSTRACT

Methods and compositions are provided for detecting nucleic acid sequences. In particular, pairs of probes are employed, where the pair defines a substantially contiguous sequence on a target nucleic acid. Each of the pairs has a side chain which forms a stem of the two side chains which non-covalently bind to is capable of forming a cross-link upon activation, when the probes and sample nucleic acid are base paired. Each of the nucleic acids is initially present as single stranded to allow for base pairing, so that the probes bind to homologous target nucleic acid. The assay mixture is activated to provide cross-linking, the double stranded nucleic acid melted, and the process of base pairing, activation and melting repeated, a sufficient number of cycles, to provide a detectable amount of cross-linked probes. Kits are provided with the appropriate reagents for carrying out the subject method.

22 Claims, No Drawings

NUCLEIC ACID SEQUENCE DETECTION EMPLOYING AMPLIFICATION PROBES

TECHNICAL FIELD

The field of this invention is nucleic acid sequence detection.

BACKGROUND

The amount of information concerning the genomes of a large variety of species is increasing exponentially. The availability of known sequences creates an enormous market for the detection of particular sequences present as DNA or RNA, whereby one can detect the presence of genes, their transcription or mutations, such as lesions, substitutions, deletions, translocations, and the like. By knowing sequences of interest, one can detect a wide variety of pathogens, particularly unicellular microorganisms and viral strains, and genetic diseases including the presence of genes imparting antibiotic resistance to the unicellular microorganisms as illustrative of only a few of the available possibilities. In addition, there are needs within the extensive areas of genetic counseling, forensic medicine, research, and the like, for nucleic acid sequence detection technology.

In many instances, the target DNA is only a very small proportion of total DNA in the sample. Furthermore, there may be many situations where the target DNA of interest and other sequences present have substantial homology. It is therefore important to develop methods for the detection of the target DNA sequence that are both sensitive and accurate.

Severable enzymatic amplification methods have been developed, such as PCR, LCR, NASBA, and SSR. The first and most notable method that has received extensive use is the polymerase chain reaction. Starting with specific primers, nucleoside thriphosphate monomers, the target strand of DNA and a polymerase enzyme, one can greatly amplify the target DNA sequence of interest. This technology is extremely powerful and has been applied to a myriad of research applications, but it has a number of drawbacks which limit its use in a variety of areas. General availability is limited by the restrictive nature of licenses by the owners of the patent rights. In addition, the method requires an enzyme. While the availability of thermally stable enzymes has greatly enhanced the applicability of the polymerase chain reaction, there is nevertheless the inconvenience that denaturation of the enzyme occurs during thermocycling. Also, the sample may include inhibitors of the enzyme requiring isolation of the nucleic acid sample free of inhibiting components. In addition, the methodology is sensitive to amplifying stray sequences, which then overwhelm the target sequence of interest, obscuring its presence. There is also the fact that the reagents are expensive and the amplified DNA usually requires verification. These comments apply equally to the other enzymatic amplified techniques noted above, such as the ligase chain reaction, NASBA, and self-sustained sequence replication.

There is, therefore, substantial interest in identifying alternative techniques which allow for the detection of specific DNA sequences and avoid the deficiencies of the other systems.

Relevant Literature

Barany, Proc. Natl. Acad. Sci. U.S.A. 88:189–193 (1991); Gautelli et al., Proc. Natl. Acad. Sci. U.S.A. 87:1874–1878 (1990).

SUMMARY OF THE INVENTION

Methods and compositions are provided for detecting nucleic acid sequences by using a pair of probes, in each of which at a different end there is a portion of the chain which serves as one half of a stem, which portion will be referred to as a side chain. The side chains comprise a cross linking system. Upon orientation of the side chains in spacial proximity as a result of binding of the probes to a contiguous homologous sequence and activation of a cross linking system associated with the side chains, the probes are joined together by a covalent linkage. The method employs adding the probes to the target DNA under conditions of base pairing, activating the cross-linking system, so that primarily only those side chains in spacial proximity form a covalent bond, melting double-stranded nucleic acid and repeating the cycle, whereby in the reannealing process the probes in addition to binding to target nucleic acid, will also bind to cross-linked probes. In this manner, one may obtain a geometric increase in the number of cross-linked probes as the cycle of steps is repeated, wherein the process is initiated solely by the presence of target DNA.

DESCRIPTION OF THE SPECIFIC EMBODIMENT

Methods and compositions are provided for detecting a nucleic acid sequence employing at least one pair of first and second probes. The pair of probes defines a target sequence, where upon base pairing of the probes to the target sequence, the probes are brought into close spacial proximity. Each of the probes has a portion of the probe, which acts as a side chain which does not bind to the target sequence. The side chains act as one-half of a stem and non-covalently interact through hydrogen bonding, salt bridges, and/or Van der Waal forces. When the stem is formed, the side chains comprise a covalent bond cross-linking system, which upon activation results in a covalent bond between the side chains, thus permanently linking the probes under the conditions of the process.

The method is performed by combining the target nucleic acid with the probes or probe sets in an appropriate medium for base pairing. The nucleic acid may be DNA or RNA, single or double stranded, or other molecule which comprises pyrimidines and/or purines capable of base pairing. After sufficient time for the probes to bind to the target nucleic acid or in subsequent steps to bind as well to cross-linked probes, the cross-linking system is activated resulting in covalent bonding between the two probes. One then melts double stranded nucleic acid to release the probes from the homologous sequence and repeats the process over again, whereby the number of cross-linked probes in the presence of target sequence is increased linearly or geometrically. Where only one pair of probes is used, linear amplification of cross-linked probes is obtained, which may be satisfactory in many instances.

In describing the subject invention, the probes will be considered first. Each of the probes will have a sequence of at least about 10, more usually at least about 15, preferably at least about 18 and usually not more than about 1 kb, more usually not more than about 0.5 kb, preferably in the range of about 18 to 200 nt, where the sequence is homologous to the target sequence. For the most part, the total number of nucleotides which are homologous to the target sequence for the two probes will be at least about 15 nt, more usually at least about 25 nt, and not more than about 1.2 kb, usually not more than about 0.5 kb, preferably not more than about 300 nt. The base pairing domains present on the target nucleic acid will normally not be separated by more than 10 nucleotides, more usually not more than about 6 nucleotides, and preferably not more than about 2 nucleotides and may be contiguous.

Each of the probes has a side chain, 3' on the first probe and 5' on the second probe in the 5'-3' direction, which will provide for non-covalent association to form a stem. Non-covalent association can be obtained by hydrogen bonding, salt bridges, Van der Waal forces, and the like, particularly hydrogen bonding. For the most part, the groups involved will have oxygen and nitrogen bonded hydrogen, e.g. purines and pyrimidines. Upon activation, covalent cross-linking between members of the stem occurs. The reaction rate occurring as a result of the spacial proximity of the side chains due to the base pairing of the probes to an homologous sequence will usually be at least about 10 fold, preferably at least about $10^2$ fold, greater than the reaction that occurs between the probes unbound to the homologous sequence.

The side chains will be selected so as to have a weak association or affinity. By weak is intended that in the absence of the target in the solution, the equilibrium between unassociated probes in solution and associated probes, due to the affinity between the side chains and target homologous nucleic acid sequences will be less than about $10^{-1}$, usually less than about $10^{-3}M^{-1}$. The affinity may be as a result of hydrogen bonding, salt formation, or other low energy event.

To obtain stem formation, conveniently, one may use paired nucleotides, at least 2, generally at least 3, and usually not more than about 20, more usually not more than about 16 base pairs, preferably not more than about 8 base pairs. Alternatively, one may use amino acids which provide for hydrogen bonding and/or salt bridges. Other hydrogen bridges may involve diamines and diol acidic groups, particularly ortho-phenolates. However, for the most part, considering convenience, ease of synthesis, control of affinity, and substantial absence of interference, nucleotides will be employed. Usually, the pairs will be A and T, where the nucleotides may be the same on one side chain or different, that is all T's on one chain and all As on the other chain, or a mixture of A's and T's on the two side chains. However, one may also use G and C, by themselves or in combination with A and T. Instead of the normal 4 or 5 natural bases (including uracil), one may use other bases or other moieties providing for hydrogen bonding and spacial orientation, such as uracil, 5-methylcytosine, 5-fluorouracil, inosine, 1-methylinosine, 3-nitropyrrole, and the like. The particular choice of nucleotide will depend on the desired affinity, ease of synthesis, interaction with the covalent cross-linking, and the like. Generally, the side chains, excluding groups bound to the chain will be at least about 20 atoms in the chain, more usually at least about 30 atoms in the chain, generally fewer than 100 atoms, more usually fewer than about 60 atoms. The atoms will be carbon, oxygen, nitrogen, sulfur, phosphorus, and the like. The cross-linking moieties may be part of the side chain or appended to the side chain, depending upon the nature of the moiety.

The base pairing sequences of the two probes will be selected so as to provide a low affinity between the two probes. Therefore, the target sequences will be selected so that there will not be a significant number of nucleotides defining a sequence of homology, particularly complementarity, between the two probes. The greater the complementarity between the two probes, the more stringent the conditions will be required during the period of activation of the cross-linking system. Therefore, one has substantial discretion in the selection of the probes in relation to the conditions employed for base pairing of the homologous sequences.

In one embodiment, one of the side chains will provide for a bulge adjacent to the homologous sequence. The bulge will be between the last nucleotide base pairing with said target sequence and directly linked to said side chain and the first group providing for non-covalent association between the side chains to form the stem, e.g. base pairing of nucleotides on respective side chains. Using nucleotides as exemplary, there will usually be 1 to 3 unpaired nucleotides, before base pairing occurs between the two side chains. Other groups may be used which provide approximately the same degree of flexibility. There will usually be only one bulge, but in some situations, one may have a bulge in each side chain.

One or both of the members involved in the cross-linking may be provided by an intermediate, which is not a nucleotide or modified nucleotide. By employing a difunctional molecule for insertion into the chain of the side chain, where the difunctional molecule carries the cross-linking agent, the members of the side chains participating in the cross-linking may be conveniently positioned for reaction. Various polyfunctional molecules may be used to provide stable participation of the cross-linking moiety in the side chain. Desirably, agents will be used which can react with a phosphorus moiety, particularly a phosphoramidite, or can form a phosphoramidite, where the linking atom may be oxygen, carbon, sulfur, or the like. Core molecules for linking a cross-linking moiety to the side chain, where the core molecule participates in the backbone of the side chain include glycerol, dithiothreitol, 1,3,5-trihydroxycyclohexane, deoxyribose, 2-hydroxymethylacrylic acid, or the like. Since the phosphorus group can be modified to react with a wide variety of functionalities, there is no significant restriction on how the core molecule is fitted into the backbone of the side chain. Phosphorus derivatives include, phosphoramidites, phosphate esters, phosphines, phosphohalides, etc.

There are extensive methodologies for providing cross-linking upon spacial proximity between the side chains of the two probes, to form a covalent bond between one member of the stem and the other member of the stem. Conditions for activation may include photonic, thermal and chemical. Any condition employed must provide for a substantial difference in the reaction rate when bound to a template sequence as compared to free in solution. This can be achieved in a wide variety of ways. One can provide concentrations where events in solution are unlikely and activation of the cross-linking group will be sufficiently short lived, so that the activated group is not likely to encounter another probe in solution. This can be tested using control solutions having known concentrations of probes and determining the formation of cross-linked probes in the presence and absence of template. One may use quenchers that act to deactivate cross-linking groups on probes that are free in solution, where the quencher may accept energy, provide a ligand to replace a lost ligand, react with the cross-linking group to inhibit cross-linking with another probe, and the like. By adjusting the amount of quencher in the medium, one can optimize the desired reaction as compared to the background reaction. One may use sensitizers, where reaction only occurs upon activation of the cross-linking moiety by transfer of energy from the sensitizer to the cross-linking moiety. The significant point is that the sensitizer, which will be bound to the other probe from the probe carrying the cross-linking moiety, is directly irradiated and the energy will be dissipated in solution in the absence of the cross-linking moiety accepting the energy.

Acceptance of the energy has a much greater probability when the side chains are involved in stem formation. Sensitizers which may be employed include biphenyl, fluorenone, biacetyl, acetonaphthone, anthraquinone, bibenzoyl, benzophenone, etc. These sensitizers find particular application with the coumarin functionality.

In one aspect, one can employ photochemistry where a single reactive species on one chain reacts with a group present on the second chain. A large number of functionalities are photochemically active and can form a covalent bond with almost any organic moiety. These groups include carbenes, nitrenes, ketenes, free radicals, etc. One can provide for a donor molecule in the bulk solution, so that probes which are not bound to a template will react with the terminating molecule to avoid cross-linking between probes. Carbenes can be obtained from diazo compounds, such as diazonium salts, sulfonylhydrazone salts, or diaziranes. Ketenes are available from diazoketones or quinone diazides. Nitrenes are available from aryl azides, acyl azides, and azido compounds. For further information concerning photolytic generation of an unshared pair of electrons, see A. Schonberg, Preparative Organic Photochemistry, Springer-Verlag, N.Y. 1968. Illustrative compounds and terminating molecules include olefins or compounds with a labile proton, e.g. alcohols, amines, etc.

For greater specificity, one may use a molecule which upon photoactivation forms a covalent bond with a specific other molecule or small group of molecules via cycloaddition or photosubstitution reaction. There are a significant number of compounds which will react with nucleic acid bases to form covalent bonds. Thymidine will react with thymidine to form a covalent link. Preferably, other compounds will be used which react with nucleic acid bases. These compounds will include functional moieties, such as coumarin, as present in substituted coumarins, furocoumarin, isocoumarin, bis-coumarin, psoralen, etc., quinones, pyrones, α,β-unsaturated acids, acid derivatives, e.g. esters, ketones, and nitriles; azido, etc.

Instead of having a reaction with a nucleotide, one can provide for two different reactants, where reaction is unlikely when the two reactants are not in proximity upon activation. Reactions of this nature include the Dieis-Alder reaction, particularly a photoactivated Dieis-Alder cyclization reaction, where a diene, and a dienophile e.g. olefin or acetylene, are employed. Reactive dienes may be employed, such as 1,4-diphenylbutadiene, 1,4-dimethylcyclohexadiene, cyclopentadiene, 1,1-dimethylcyclopentadiene, butadiene, furan, etc. Dienophiles include maleimide, indene, phenanthrene, acrylamide, styrene, quinone, etc. One may provide for sensitized activation to provide for the cyclization, using such photoactivators as benzophenones with cyclopentadiene, which may react with another cyclopentadene molecule, or a different dienophile. Alternatively, one may employ addition of ketones to olefins, as in the case of benzophenone and isobutylene or 2-cyclohexenone.

Another class of photoactive reactants are organometallic compounds based on any of the d- or f-block transition metals. Photoexcitation induces the loss of a ligand from the metal to provide a vacant site available for substitution. Placement of the organometallic compound on one side chain and a suitable ligand, on the other chain provides a system which relies on the proximity of the two chains for the cross-linking to occur. Suitable ligands may be the nucleotide itself or other moieties, such as amines, phosphines, isonitriles, alcohols, acids, etc. For further information regarding the photosubstitution of organometallic compounds, see "Organometallic Photochemistry," G. L. Geoffrey, M. S. Wrighton, Academic Press, San Francisco, Calif., 1979.

One may also employ active monomers which can dimerize with a second monomer, such as styrene, acrylonitrile, vinyl acetate, acenaphthylene, anthracene, etc. By activating one of the monomers photolytically, the activated monomer can react with the other monomer on the other side chain. Particularly, by using two different monomers, where the second monomer provides for a more stable active species than the first monomer, one may include a quencher in the reaction medium so as to quench the active intermediate. In some instances, the intermediate will self-quench by elimination or other suitable reaction. One may also provide for photolytically activated homolytic or heterolytic cleavage, such as active halides, e.g. benzyl halides, particularly bromo and iodo, where upon cleavage, the active molecule would act with a recipient molecule, such as an olefin which would provide for addition of the carbon and halogen across the double bond.

Other reactions which might be employed include photonucleophilic aromatic substitution.

Thermal activation may also be employed, but is less desirable in many cases since until the temperature is lowered, the reactive species is maintained. Therefore, this will usually require lower concentrations of at least one of the probes, the ability to rapidly change the temperature of the system, and the selection of reactants which provide for a high energy barrier for reaction in the absence of spacial proximity. Reactions which may be employed include many of the ones described above for photolytic activation, such as Dieis-Alder reactions, covalent bond scission and addition across a double bond, epoxide ring-opening.

Also, chemical reactions can be employed where one provides for cycling of the active moiety in the absence of reaction with the recipient reactant. Thus, one can provide for a redox couple, such as ferrous and ferric ions, where the active species free in solution would normally be inactivated prior to encountering the recipient compound. For example, one could have a hydroperoxide as the reactant species and an active olefin as the recipient. Upon reduction of the hydroperoxide, a free radical can be obtained which can react with the electron donor compound, which can then be further reduced to a stable compound.

Any of the various groups indicated may be modified by replacement of a hydrogen with a functionality or convenient linking group for attachment to the backbone of the side chain. These functionalities will, for the most part, be oxy, oxo, amino, thio, and silyl.

The probe homologous sequence which binds to the template will usually be naturally occurring nucleotides, but in some instances the phosphate-sugar chain may be modified, by using unnatural sugars, by substituting oxygens of the phosphate with sulphur, carbon, nitrogen, or the like, or other modification which can provide for synthetic advantages, stability under the conditions of the assay, resistance to enzymatic degradation. The homologous sequence will usually have fewer than 10 number % of the nucleotides different from the target sequence, and usually the lesser of 10 number % and 10 nucleotides, more usually 5 nucleotides. The relationship of the pairs of probes will usually come within the same limitations, but will more usually be complementary, that is, have perfect nucleotide pairing. Differences between sequences may include insertions, deletions, and substitutions, i.e. transitions and transversions. If one wishes one may have more than one set of probes specific for a target sequence, but may simultaneously have 2 or more sets of probes, usually not more than 10 different sets, more usually not more than about 5 different sets, directed to different target sequences. A probe set is two pairs of probes, where the probes have homologous binding sequences, so as to bind to target sequence and to each other. Where one has a plurality of probe sets, each of the probe sets will have to be distinguishable in some assay, for example, by size difference, different label, etc.

In some instances it may be desirable to provide three different probes, where three probes define three contiguous sequences and two stems, the middle probe having two side chains, so as to interact with each of the other side chains of the other two probes. This can be particularly useful with regions of polymorphism, where the central probe is directed to a conserved region, and one of both of the other probes are directed to polymorphic regions. One may then use a plurality of probes, one for each of the polymorphic regions, where cross-linking will result for any of the polymorphic sequences being present.

The probes may be prepared by any convenient synthetic scheme. In one scheme, the side chains may be prepared first, followed by being linked to the sequence homologous to the target sequence. The synthesis of the side chains will depend, of course, on the nature of the pairing groups. For oligonucleotides, conventional manual or automated techniques may be employed. One or more of the monomers may comprise a cross-linking group. By employing a linker in the backbone which employs a dexoyribosyltriphosphate group or can substitute for the deoxyribosyltriphosphate group, the cross-linking containing group may be readily inserted into the backbone during the synthesis. The side chains may have terminal functionalities that allow for direct linkage of the sequence homologous to the target sequence, e.g. a nucleotide 5'-triphosphate or nucleotide having a free 3'-hydroxyl. The homologous sequence may be joined by ligation, by using the side chains in conjunction with a primer for PCR, or other linking means. The side chains may be used to terminate a chain being produced on a bead or may be the initiating group bound to the bead by a cleavable linker. Thus side chains can be provided as reagents for use in automated synthesis, where the side chains will provide the initiating or terminating reagent. Various attachment groups may be provided for the side chain, where the side chain is to be attached to a bead. Functionalities on the bead can be hydroxy, carboxy, iminohalide, amino thio, active halogen or pseudohalogen, carbonyl, silyl, etc. For ease of removal from the bead, various linkers may be employed which will include groups, such as benzhydryl ethers, acetals, including sulfur analogs thereof, o-nitrobenzyl ether, 7-nitroindanyl, cyclic anhydrides, polypeptides having a sequence recognized by a peptidase, silanyl, β-(electron withdrawing group) substituted esters, or the like. The particular linking group which is selected will depend upon the nature of cross-linking group and the manner in which it is bonded to the side chain backbone.

Of particular interest are compositions which provide the side chains and can be joined to sequences homologous to target sequences, to provide probes, where the compositions are of the following formula:

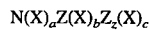

$N(X)_a Z(X)_b Z_x(X)_c$ wherein:

N is a moiety capable of ligation to a nucleotide, which may comprise an hydroxyl group, a phosphate group, a triphosphate group, or the like, including nucleosides, nucleotides, phosphoramidites, phosphate esters, sugars, hydroxyalkyl or -aryl groups, and the like;

X is a nucleotide, naturally occurring or synthetic, capable of hydrogen bonding to another nucleotide, preferably at least one X will be adenosine, more usually at least about 50% of the X's will be adenosine, when Z reacts with thymidine;

Z is a linking group having as a side chain a moiety capable of cross-linking with another moiety, particularly with a nucleotide, more particularly as a result of photoactivation (see groups described above); or a sensitizer (see groups described above); Z will usually be of at least about 8 atoms other than hydrogen, more usually at least about 10 atoms other than hydrogen, and not more than about 50 atoms, more usually not more than about 36 atoms other than hydrogen, where Z may be aliphatic, alicyclic, aromatic, heterocyclic, or combinations thereof, where cyclic having from about 1 to 3 rings, which may be fused or non-fused, composed of carbon, oxygen, nitrogen, sulfur and phosphorus, comprising functional groups, such as oxy, oxo, amino, thio, cyano, nitro, halo, etc., usually having at least one heteroatom, more usually at least about 3 heteroatoms, and not more than about 10 heteroatoms;

a, b and c are integers of a total in the range of 2 to 20, where a and c are at least one;

x is 0 or 1.

The side chain compositions described above are used in conjunction with a second side chain for linking to a sequence homologous to the target sequence. Either of the side chain compositions can be selected for linking to the 3' or 5' terminus of the homologous sequence. The second side chain will have nucleotides complementary to the nucleotides of the first chain to provide hydrogen bonding. In the simplest second chain, it may be a poly-T, where the cross-linking group reacts with thymidine, and the nucleotides in the first chain are adenosine. Where the first chain has other than adenosine bases, the second chain will have the complementary bases. The first and second side chains can be provided as reagents for linking to the homologous sequences, as termini of primers for PCR to provide the probes directly, or the like.

In addition, one or both of the side chain compositions may terminate with a label which allows for detection, such as a radiolabel, fluorescer, chemiluminescer, or the like, for detection of the cross-linked probes.

In carrying out the assay, the sample may be subjected to prior treatment. The sample may be a cellular lysate, isolated episomal element, e.g. YAC, plasmid, etc., virus, purified chromosomal fragments, cDNA generated by reverse transcriptase, mRNA, etc. Depending upon the source, the nucleic acid may be freed of cellular debris, proteins, DNA, if RNA is of interest, RNA, if DNA is of interest, size selected, gel electrophoresed, restriction enzyme digested, sheared, fragmented by alkaline hydrolysis, or the like.

For linear expansion, only one set of probes is required. After each melting step, linked probes will be obtained in proportion to the amount of target DNA present. For geometric expansion, two pairs of probes will be used. Where the target sequence is a single strand, the initial pair would be homologous to the target and the pair having the analogous sequence to the target added after concommitantly or after the first cycle of cross-linking. Where the sample is double stranded, then both pairs of probes, a pair for each strand, are added initially.

The probes and template will be brought together in an appropriate medium and under conditions which provide for the desired stringency. Therefore, usually buffered solutions will be employed, employing salts, such as citrate, sodium chloride, tris, EDTA, EGTA, magnesium chloride, etc. See, for example, Molecular Cloning: A Laboratory Manual, eds. Sambrook et al., Cold Spring Harbor Laboratory, Cold Spring Harbor, N.Y., 1988, for a list of various buffers and conditions, which is not an exhaustive list. Solvents may be water, formamide, DMF, DMSO, HMP, alkanols, and the like, individually or in combination, usually aqueous solvents. Temperatures may range from ambient to elevated temperatures, usually not exceeding about 100° C., more usually not exceeding about 90° C. Usually, the temperature for photochemical and chemical cross-linking will be in the range of about 20° to 60° C. For thermal cross-linking, the temperature will usually be in the range of about 70° to 120° C.

The ratio of probe to target nucleic acid may be varied widely, depending upon the nature of the cross-linking agent, the length of the homology between the probe and the target, the differences in the nucleotides between the target and the probe, the proportion of the target nucleic acid to total nucleic acid, the desired amount of amplification, or the like. The probes will usually be about at least equimolar to the target and usually in substantial excess. Generally, the probes will be in at least 10 fold excess, and may be in $10^6$ fold excess, usually not more than about $10^{12}$ fold excess, more usually not more than about $10^9$ fold excess in relation to the target during the first stage. The initial ratio of probes to target nucleic acid may be maintained during successive cycles or may be allowed to diminish by the amount of reaction of the reactive species. The ratio of one probe to the other may also be varied widely, depending upon the nature of the probes, the differences in length of the homologous sequences, the binding affinity of the homologous sequences to the target sequence, the role of the probe in the cross-linking system, and the like. Conveniently, the probes may be equimolar, but may vary in the range of 1:1–20 more frequently, 1:1–10, where, when there is only one reactive or activated species, the reactive side chain will usually be in excess to substantially ensure that the reactive probe is bound to the template, when the unactivated probe is present on the template.

Where the sample is double stranded, it will usually be denatured, where denaturation can be achieved chemically or thermally. Chemical denaturation may employ sodium hydroxide in an appropriate buffered medium, e.g., tris-EDTA(TE). While triplex formation may be employed, particularly by complexing the probes with RecA, there will generally be no advantage to such a protocol and it requires the continuous presence of natural or active RecA.

During the course of the reaction, depending upon how the assay is carried out, there may be significant evaporation. Therefore, it will normally be desirable to put a coating over the assay medium which inhibits evaporation. Various heavy oils may find use, such as mineral oil, silicone oil, vegetable oil, or the like. Desirably, the oil should be free of any contaminants which might interfere with the assay. Alternatively, one may use sealed systems, where evaporation is inhibited.

The amount of target nucleic acid in the assay medium will generally range from about 0.1 yuctomol to about 100 pmol, more usually 1 yuctomol to 10 pmol. The concentration of sample nucleic acid will vary widely depending on the nature of the sample. Concentrations of sample nucleic acid may vary from about 0.01 fM to 1 μM. In fact, the subject method has the capability to detect a single molecule in the absence of significant interference. The amount of the probes may be varied and their concentration varied even more widely, in that there will usually be at least about an equimolar amount of the probes and as indicated previously, large excesses of one or the other or both of the probes may be present. Where the target is single stranded, one may initially use substantially less of the probe in relation to the target since there is no competition between the probes and an homologous sequence for the target. Where the target is double stranded, initially, one will normally use more of the probes so as to enhance the competitive advantage of the probes for the complementary sequences as against the target sequences of the sample.

Where chemical denaturation has occurred, normally the medium will be neutralized to allow for hybridization. Various media can be employed for neutralization, particularly using mild acids and buffers, such as acetic acid, citrate, etc., conveniently in the presence of a small amount of an innocuous protein, e.g. serum albumin, β-globulin, etc., generally added to provide a concentration in the range of about 0.5 to 2.5%. The particular neutralization buffer employed is selected to provide the desired stringency for the base pairing during the subsequent incubation. Conveniently the stringency will employ about 1–10×SSC or its equivalent. The base pairing may occur at elevated temperature, generally ranging from about 20° to 65° C., more usually from about 25° to 60° C. The incubation time may be varied widely, depending upon the nature of the sample in the probes, generally being at least about 5 min and not more than 6 h, more usually at least about 10 min and not more than 2 h.

After sufficient time for the base pairing to occur, the reactant may be activated to provide cross-linking. The activation may involve light, heat, chemical reagent, or the like. The particular wavelength which is employed may vary from about 250 to 650 nm, more usually from about 300 to 450 nm. The intensity will depend upon the particular reaction and may vary in the range of about 0.5 W to 250 W. In order to obtain amplification, it will now be necessary to melt probes bound to the template. Melting can be achieved most conveniently by heat, generally heating to at least about 60° C. and not more than about 100° C., generally in the range of about 65° C. to 95° C. for a short period of time, frequently less than about 5 min, usually less than about 2 min, and normally for at least about 0.1 min, more usually for at least about 0.5 min. While chemical melting may be employed, it is inefficient and will only be used in special circumstances, e.g. thermal activation. After the melting, the medium will usually be cooled by at least about 20° C., sometimes 30° C. or more, generally bringing the temperature of the assay medium to a temperature in the range of about 20° C. to 75° C. during which time annealing may occur.

Activation may then be initiated immediately, or after a short incubation period, usually less than 1 h, more usually less than 0.5 h. With photoactivation, usually extended periods of time will be involved with the activation, where incubation is also concurrent. The photoactivation time will usually be at least about 1 min and not more than about 2 h, more usually at least about 5 min and not more than about 1 h. During the incubation and photoactivation, the temperature will be dropped to below about 60° C., usually below about 50° C. and may be as low as 10° C., usually being at least about 30° C. This process may be repeated if desired, so that the melting-annealing and photoactivation may occur with from 1 to 40 cycles, more usually from 1 to 30 cycles, preferably from 1 to 25 cycles. During the cycles, the amount of probe may be replenished or enhanced as one proceeds. The enhancement will usually not exceed about five fold, more usually not exceed about two fold.

As the reaction proceeds, in the case of linear expansion, at each stage there will be hybridization with the target and additional linked probes formed in relation to the amount of target DNA. For geometric expansion, if the original target was single stranded, in the first cross-linking step, there will be the target nucleic acid as a template and the cross-linked nucleic acid, which can now serve as a template for the probes having the same sequence as the target nucleic acid. In the next stage, one will now produce templates of probes having the same sequence as the target and the homologous sequence as the target. Thereafter, for each subsequent cycle, one will form cross-linked probes on the target sequence template, as well as on the two different cross-linked probe templates. The situation is analogous with double stranded nucleic acid, except that in the first step one needs to provide probes for both target templates and there is an initial geometrical expansion as to both of these probe sequences.

The resulting composition will comprise cross-linked probes. Such composition may be used as probes to identify homologous sequences, to isolate target sequences having homologous sequences, and the like. The composition finds particular use in identifying the presence of the target sequence in the sample.

At the end of the iterations, the presence and amount of cross-linked probes may be determined in a variety of ways. Conveniently, gel electrophoresis may be employed and the amount of cross-linked probes determined by the presence of a radioactive label on one of the probes using autoradiography; by staining the nucleic acid and detecting the amount of dye which binds to the cross-linked probes; by employing an antibody specific for the dimerized probe, particularly the cross-linked area, so that an immunoassay may be employed; or the like.

If desired, for quantitation, an internal control may be provided, where a known amount of a known sequence is introduced, with a known amount of probes, equivalent to the probes for the target sequence of interest. By carrying out the assay, one would obtain linked probes from the control and linked probes related to any target sequence present in the sample. By taking aliquots of the assay medium during the assay and after each or different numbers of cycles, one can determine the efficiency of the assay conditions, as well as ratios of cross-linked control probes to cross-linked sample probes. If one has an estimate of the amount of sample DNA which should be present, one can terminate the assay once the amount of cross-linked control probe indicates that there should be sufficient cross-linked sample probe to be detectable. By having a fluorescent molecule on one side chain and a quencher molecule on the other side chain, one can monitor the degree of cross-linking in relation to the change in fluorescence of the assay medium.

Instead of separating the probes from the assay medium, detection techniques can be employed which allow for detection during the course of the assay. For example, each of the probes may be labeled with different fluorophores, where the energy of the emitted light of one of the fluorophores is in the absorption band of the other fluorophore. In this way, there is only energy transfer when the two fluorophores are in close proximity. See, for example, U.S. Pat. Nos. 4,174,384, 4,199,599 and 4,261,968. By exciting a first fluorophore at a wavelength which does not excite the second fluorophore, where the first fluorophore emits at a wavelength absorbed by the second fluorophore, one can obtain a large Stokes shift. One reads the fluorescence of the second fluorophore, which is related to the number of first and second fluorophores which are in propinquity. During the course of the assay, at the end of each cycle, one can determine the fluorescence of the medium at the emission wavelength of the second fluorophore as a measure of the amount of cross-linking and indicative of the presence of the target sequence and its amount. To provide a more quantitative measurement, one can use controls having a known amount of target sequence and compare the fluorescent signals observed with the sample and control.

By virtue of the fact that one is linking two probes, one can use different labels on the different probes to allow for detection of cross-linking. Since the two labels will not be held together except when the two probes are cross-linked, one can use the existence of the two labels in a single molecule to measure the cross-linking. For example, by having one label which is a member of a specific binding pair, e.g. antibody and ligand, such as digoxigenin and anti-digoxigenin, biotin and streptavidin, sugars and lectins, etc., and having the other label providing a detectable signal either directly or indirectly, one has the opportunity to separate the cross-linked probes on a solid support, e.g. container surface or bead, e.g. magnetic bead, where the detectable label becomes bound to the solid support only when part of the cross-linked probes. For direct detection, one may have fluorophores, chemiluminescers, radiolabels, and the like. For indirect detection, one will usually have a ligand which binds to a reciprocal member, which in turn is labeled with a detectable label. The detectable label may be any of the above labels, as well as an enzyme, where by adding substrate, one can determine the presence of cross-linked probe.

Where one has ternary probes, particularly with a polymorphic target, a central probe to a conserved region and outer probes for the polymorphic regioins, one can use differentially detectable labels on the outer probes and a ligand on the central probe for separation. In this way, one can readily determine which polymorphism(s) are present. The separation of the cross-linked probes provides the advantage of isolation of the cross-linked probe from the uncross-linked probe carrying the label, allows for washing of the bound probe, and removal of non-specifically bound label. Thus, background due to uncross-linked lable can be diminished.

For carrying out the methodology, various heating and cooling systems may be employed, such as a thermal cycler, regulated temperature baths, and the like.

Kits are provided having at least two pairs of probes, or ternary combinations of probes, where each pair may be in the same vessel. At least one pair will define a substantially contiguous sequence of a target nucleic acid and the other pair will be homologous, usually complementary, to the sequence of the first pair. Each probe has a side chain which forms a stem with the side chain of the other pair, so as to be capable of cross-linking as described previously. If desired, one or both of the probes may be labeled to allow for easy detection of cross-linked probes. One may use radioactive labels, fluorescent labels, specific binding pair member labels, and the like.

The following examples are offered by way of illustration and not by way of limitation.

EXPERIMENTAL

Sequences of Nucleic Acids

Nax 228 (SEQ ID NO:01) 5'ATTTTGTCTTTGCGCA-CAGACGATCTATTT3'

Nax 229 (SEQ ID NO:02) 3'TTTCGTTTGTCTGCTA-GATAAA5'

Nax 230 (SEQ ID NO:03) 3'TAAAACAGAAACGCGC-GAXA5'

Nax 231 (SEQ ID NO:04) 5'ATTTTGTCTTTGCGCG-GCTTT3'

Nax 232 (SEQ ID NO:05) 3'AXACGTTTGTCTGCTA-GATAAA5'

Nax 233 (SEQ ID NO:06) 3'TAAAACA-GAAACGCGCGTTT5'

X=O=glyceryl coumarin

1. The ability to obtain cross-linking with a photoactivatable probe was investigated.

| Component, Nax | pm/µl* | Sample, µl | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| $^{32}$P-228 | 0.5 | 2 | 2 | | | | | | | 2 | | | | | | | |
| $^{32}$P-229 | " | | | 2 | 2 | 2 | 2 | | 2 | | 2 | 2 | 2 | | | | |
| $^{32}$P-233 | " | | | | | | | 2 | | | | | | | 4 | 4 | 4 | 4 |
| 228 | " | | | | | | | | 2 | | | | | | | | 2 | 2 |
| 229 | " | | 2 | | 2 | | | | | | | | | | | | |
| 230 | " | | | 2 | 2 | | | 2 | 2 | | | | | | | | |
| 232 | " | | | | | | | | | | 2 | | 2 | | 2 | | 2 |
| 233 | " | | | | | | | | | | | 2 | 2 | | | | |
| H$_2$O | | 1 2 | 1 0 | 1 0 | 8 | 1 2 | 1 0 | 1 0 | 8 | 1 2 | 10 | 10 | 8 | 10 | 8 | 8 | 6 |

*pmol/µl
Total volume = 32.5 µl

Protocol

Add 18.5 µl of 50:150 0.75M NaOH: 1 xTE to 14 µl of sample.

Incubate at r.t. for 10 min.

Add 17.5 µl neutralization buffer: 3.5 µl of 3.5% BSA; 1.5 µl of 1.5M HOAc; 11.3 µl of 20×SSC and 0.4 µl of water.

Incubate at 40° C. for 15 min.

Irradiate at 30° C. for 1 h (Stratalinker; thin pyrex filter)

PAGE 15% (with 7M urea)

The results of the PAGE showed that samples 3, 8 and 10 showed good cross-linking, but the band for sample 16 was light as compared to the other bands.

2. The effect of thermal cycling on cross-linking was investigated.

| Component, Nax | pm/µl* | Sample, µl | | | | | | | |
|---|---|---|---|---|---|---|---|---|---|
| | | 1 | 2 | 3 | 4 | 5 | 6 | 7 | 8 |
| $^{32}$P-229 | 1 | 1 | 1 | 1 | 1 | | | | |
| $^{32}$P-233 | " | | | | | 1 | 1 | 1 | 1 |
| 228 | 0.02 | | 1 | | 1 | | 1 | | 1 |
| 230 | 0.5 | 2 | 2 | 2 | 2 | | | | |
| 232 | " | | | | | 2 | 2 | 2 | 2 |
| H$_2$O | | 11 | 10 | 11 | 10 | 11 | 10 | 11 | 10 |

*pmol/µl
Total volume = 32.5 µl

Protocol

Add 18.5 µl of 50:150 0.75M NaOH: 1 xTe to 14 µl of sample.

Incubate at r.t. for 10 min.

Add 17.5 µl neutralization buffer: 3.5 µl of 3.5% BSA; 1.5 µl of 1.5M HOAc; 11.3 µl of 20×SSC and 0.4 µl of water.

Incubate at 40° C. for 15 min.

Irradiate at 40° C. for 25 min (Stratalinker; thin pyrex filter)

Remove samples, 3,4,7,8; put in thin wall PCR tubes, heat to 88° C. for 1 min.

Cycle:

Irradiate at 30° C. for 25 min.

Remove samples, heat to 88° C. for 1 min.

Repeat cycle 3x ending with irradiation

PAGE 17% (with 7M urea)

Based on the PAGE results, samples 1, 3, 5, and 7 showed that with or without thermocycling, in the absence of the target strand, the two probes do not significantly cross-link. Cross-linking was more efficient with probes 29 and 230. The extent of cross-linking was quantified for samples 2 and 4, where cross-linking was 2.3% and 7.8% respectively.

Sequences of Nucleic Acids

Nax 238 (SEQ ID NO:07) 5'TTTATAAAAAGCTCG-TAATATGCAAGAGCATTGTAAGCAGAAGACTTA3'

Nax 271 (SEQ ID NO:08) 5'TTTATAAAAAGCTCG-TAATATGCTTTTTTTT3'

Nax 270 (SEQ ID NO:09) 3'TTTTTTTTTCTCGTAA-CATTCGTCTTCTGAAT5'

Nax 272 (SEQ ID NO:15) 3'AAATATTTTTCGAGCAT-TATACGAXA5'

Nax 273 (SEQ ID NO:10) 3'AAATATTTTTCGAGCAT-TATACGAAAXA5'

Nax 274 (SEQ ID NO:11) 3'AAATATTTTTCGAGCAT-TATACGAAXAAAA5'

Nax 275 (SEQ ID NO:12) 3'AAATATTTTTCGAGCAT-TATACGAAAAAXA5'

Nax 239 (SEQ ID NO:13) 3'AAATATTTTTCGAGCAT-TATACGTTCTCGTAACATTCGTCTTCTGAAT5'

Nax 278 (SEQ ID NO:14) 3'TAAATATTTTTCGAGCAT-TATACGTTCAAGTAACATTCGTCTTCTGAAT5'

Nax 277 (SEQ ID NO:16) 3'AAATATTTTTCGAGCAT-TATACGTTCTTTTTTTTT5'

Nax 276 (SEQ ID NO:17) TTTTTTTTTCATTGTAAG-CAGAAGACTTA3'

Nax 279 (SEQ ID NO:18) 5'TTTATAAAAAGCTCG-TAATATGCAAGAAXAAAA3'

Nax 280 (SEQ ID NO:19) 5'TTTATAAAAAGCTCG-TAATATGCAAGAXAAAAA3'

3. The effect of having the reactive group at the 5' terminus was investigated.

| Component, Nax | pm/µl* | 1 | 2 | 3 | 4 | 5 | 6 | 7 | 8 | 9 | 10 | 11 | 12 |
|---|---|---|---|---|---|---|---|---|---|---|---|---|---|
| ³²P-270 | 0.5 |  |  |  |  |  |  |  | 2 |  |  |  | 2 |
|  |  |  | 2 | 2 |  |  |  |  | 2 |  | 2 |  |  |
| 238 | " |  |  | 1 |  |  | 1 |  |  | 1 |  |  | 1 |
| 271 | " | 2 |  |  | 2 |  |  |  |  | 2 |  |  |  |
|  |  |  |  |  |  |  | 2 |  |  |  |  |  |  |
| 272 | " | 1 | 1 | 1 |  |  |  |  |  |  |  |  |  |
| 273 | " |  |  |  | 1 | 1 | 1 |  |  |  |  |  |  |
| 274 | " |  |  |  |  |  |  | 1 | 1 | 1 |  |  |  |
| 275 | " |  |  |  |  |  |  |  |  |  | 1 | 1 | 1 |
| H₂O |  |  |  |  | 9 |  |  | 9 |  | 11 | 9 |  | 9 |
|  |  | 11 | 11 |  | 11 | 11 | 11 |  | 11 |  |  | 11 | 11 |

*pmol/µl  
Total volume = 32.5 µl

Protocol

Add 18.5 µl of 50:150 0.75M NaOH: 1 xTE to 14 µl of sample into 96 well CoStar.

Incubate at r.t. for 10 min.

Add 17.5 µl neutralization buffer: 3.5 µl of 3.5% BSA; 1.5 µl of 1.5M HOAc; 11.3 µl of 20×SSC and 0.4 µl of water.

Add 75 µl mineral oil to inhibit evaporation.

Incubate at 40° C. for 20 min.

Irradiate at 40° C. for 20 min. (UV-A lamp, UV-32 Hoya filter)

PAGE 20% with 7M urea.

The percent cross-linking with the reactive entity at the 5' terminus was: 1, 80%; 3, 69%; 4, 57%; 6, 69%; 7, 68%; 9, 80%; 10, 38%; and 12, 67%. There was no significant cross-linking observed where there was no template.

4. The effect of having the reactive group at the 3' terminus was investigated.

| Component, Nax | pm/µl* | 1 | 2 | 3 | 4 | 5 | 6 | 7 | 8 |
|---|---|---|---|---|---|---|---|---|---|
| ³²P-276 | 0.5 |  |  | 2 | 2 | 2 |  | 2 | 2 | 2 |
| ³²P-277 | " | 2 |  |  |  | 2 |  |  |  |
| 239 | " |  |  | 1 |  |  |  | 1 |  |
| 278 | " |  |  |  | 1 |  |  |  | 1 |
| 279 | " | 1 | 1 | 1 | 1 |  |  |  |  |
| 280 | " |  |  |  |  |  | 1 | 1 | 1 | 1 |
| H₂O |  |  | 11 | 11 | 10 | 10 | 11 | 11 | 10 | 10 |

*pmol/µl  
Total volume = 32.5 µl

Protocol

The protocol was the same as the previous example, except that the PAGE was 18%.

The percent cross-linking with the reactive entity at the 3' terminus was: 1, 86%; 3, 73%; 4, 83%; 5, 79%; 7, 42%; and 8, 77%. There was no significant cross-linking observed where there was no template.

5. The time dependency of cross-linking efficiency was determined.

| Component, Nax | pm/µl* | 1 | 2 | 3 | 4 | 5 | 6 | 7 | 8 |
|---|---|---|---|---|---|---|---|---|---|
| ³²P-270 | 0.5 | 2 |  | 2 |  | 2 |  | 2 |  |
| ³²P-276 | " |  | 2 |  | 2 |  | 2 |  | 2 |
| 238 | 5 | 1 |  | 1 |  | 1 |  | 1 |  |
| 274 | " | 1 |  | 1 |  | 1 |  | 1 |  |
| 278 | " |  | 1 |  | 1 |  | 1 |  | 1 |
| 279 | " |  | 1 |  | 1 |  | 1 |  | 1 |
| H₂O |  | 10 | 10 | 10 | 10 | 10 | 10 | 10 | 10 |

*pmol/µl  
Total volume = 32.5 µl

Protocol

The above protocol was followed to the incubation at 40° C. for 15 min, where irradiation was then carried out for 20 min, with samples 1 and 2 being removed after 5 min, 3 and 4 after the next 5 min, and so on, followed by PAGE 20% with 7M urea.

The percent cross-linking observed was: sample 1, 65%; 2, 72%; 3, 76%; 4, 80%; 5, 80%; 6, 83%; 7, 82%; and 8, 84%. The odd-numbered samples had the reactive group on the 5' terminus, while the even numbered samples had the reactive group on the 3' terminus. The results indicate that after 10 min there does not seem to be any change in the degree of cross-linking and that there is no significant difference in result, whether the reactive group is on the 5' or 3' terminus.

6. The effect of variation in concentration of the probes was investigated.

| Component, Nax | pm/µl* | 1 | 2 | 3 | 4 | 5 | 6 | 7 | 8 |
|---|---|---|---|---|---|---|---|---|---|
| ³²P-276 | 0.5 | 2 | 2 | 2 | 1 | 1 | 1 | 1 | 1 |
| 278** |  | 1 | 2 | 2 | 2 | 1 | 5 | 2.5 | 1 |
| 279 | 0.5 | 2 | 2 | 2 | 2 | 2 | 2 | 2 | 2 |
| H₂O |  | 10 | 8 | 8 | 9 | 10 | 6 | 8.5 | 10 |

*pmol/µl  
Total volume = 32.5 µl  
**278 was 5 pmol/µl for sample 1, 0.5 pmol/µl for samples 2–5, and 0.02 pmol/µl for sample 6 to 8.

Protocol

The sample was prepared as previously described, followed by incubation at 40° C. for 10 min. Samples 1 and 2 were removed from the plate and put in Robbins Scientific PCR tubes (clear) and capped. The PCR tubes were laid across the top of a 96-well plate and irradiated 20 min (UV-A, UV-32). The samples were analyzed with PAGE 20% with 7M urea.

The degree of cross-linking observed in the samples was as follows: sample 1, 83%; 2, 81%; 3, 79%, 4, 82%; 5, 78%; 6, 17%; 7, 8.2%; and 3.9%. At 0.1pmol of the probe, the degree of cross-linking has significantly diminished, but even at 0.05 pmol, cross-linking is still discernible. The effect results from a combination of a lower concentration of the probe and lower mole ratio of the probe to template.

7. The use of cross-linked probes as a template was investigated.

The cross-linked products were prepared on a preparative scale and purified and isolated using PAGE. The two cross-linked products were 270–274 and 276–279.

| Component, Nax | pm/µl* | 1 | 2 | 3 | 4 | 5 | 6 | 7 | 8 | 9 | 10 | 11 | 12 |
|---|---|---|---|---|---|---|---|---|---|---|---|---|---|
| ³²P-270 | 0.5 |  |  |  |  |  | 1 |  |  | 1 |  |  | 1 |
|  |  |  |  |  |  |  |  |  |  |  | 1 | 1 |  |
| 276 | " |  | 1 | 1 | 1 |  |  |  |  |  |  |  |  |

-continued

| Component, Nax | pm/μl* | Samples, μl | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 270–274 | " | 1 | 1 | | | | | | | | | | |
| 276–279 | " | | | | | | | 1 | | | | | |
| 270 | 5 | | | | | | 1 | | | | | | |
| 274 | " | | | | | 1 | | | 1 | | | | |
| | | | | | | | 1 | 1 | | | | | |
| 272 | " | | | | | | | | | | 1 | | |
| 273 | " | | | | | | | | | | | 1 | |
| 275 | " | | | | | | | | | | | | 1 |
| 238 | " | | | | | | 1 | | | | | | |
| 276 | " | | 1 | | | | | | | | | | |
| 279 | " | 1 | 1 | 1 | 1 | | | | | | | | |
| 280 | " | | | | | 1 | | | | | | | |
| 278 | " | | | | | | 1 | | | | | | |
| 270–274 | " | | | | 1 | | 1 | | | | | | |
| 276–279 | " | | | | | | | | 1 | | 1 | 1 | 1 |
| H₂O | | | 11 | | | | | | | | 11 | | |
| | | 12 | 11 | | 11 | 11 | 12 | 11 | 11 | 11 | 11 | 11 | |

*pmol/μl
Total volume = 32.5 μl

Protocol

The samples were prepared as previously described, except only 70 μl of mineral oil was employed. The samples were incubated at 40° C. for 15 min. The samples were then irradiated at 40° C. for 20 min, followed by analysis with PAGE 14% with 7M urea.

The percent cross-linking as a result of the cross-linked probes acting as a template is as follows: sample 1, 36%; 2, 31%; 3, 18%; 4, 83%; 5, 8%; 6, 22%; 7, 26%; 8, 8%; 9, 76%; 10, 5.4%; 11, 8.8%; and 12, 14.1%. The results demonstrate that the cross-linked probes can serve as a template for cross-linking of bound probes, by themselves or in conjunction with a template molecule.

8. Linear amplification is demonstrated in the following two exemplifications.

| Component, Nax | pm/λ* | Samples, μl | | | | | | | |
|---|---|---|---|---|---|---|---|---|---|
| | | 1 | 2 | 3 | 4 | 5 | 6 | 7 | 8 |
| ³²P-276 | 0.5 | 1 | 1 | 1 | 1 | 1 | 1 | 1 | 1 |
| 278 | .005 | 1 | 1 | 1 | 1 | 1 | 1 | 1 | # |
| 279 | 0.5 | 2 | 2 | 2 | 2 | 2 | 2 | 2 | 2 |
| H₂O | | 1 | 1 | 1 | 1 | 1 | 1 | 1 | 1 |
| | | 0 | 0 | 0 | 0 | 0 | 0 | 0 | 1 |
| Conditions | | | | | | | | | |
| No. irradiations | | 1 | 5 | 5 | 1 | 1 | 1 | 1 | 1 |
| | | | | | 0 | 0 | 5 | 5 | 5 |
| Heat treatment | | | Δ | + | Δ | + | Δ | + | + |

*pmol/λ;
add 0.2λ of 0.5pmol/λ after 10 irradiations
Δ heat cycle set forth below;
+ isothermal Protocol The samples were prepared as previously described, with the probes at 100-fold excess over the target sequence.

The reagents were combined in 0.2 ml PCR tubes from MJ Research and covered with 60 μl mineral oil.

All incubations were done on a PTC-100 thermal controller from MJ Research.

The assay mixture was incubated at 40° C. for 15 min. Irradiation was for 15 min (Autoprobe, 40° C., UV-A, UV-32).

Samples 2, 4, and 6 were treated in PTC-100 (Program name PCA 8640, 4 min at 86° C.; 11 min at 40° C.)

Samples 3, 5, 7, 8 were left at room temperature.

The irradiation was repeated, with samples 2, 3 being removed after 5 irradiations, cycling continued, but with the following schedule: irradiation time: 5 min; heating time: 2 min at 86° C.; incubation time: 5 min at 40° C.

Some cloudiness was observed in samples 4 and 6 after the 6th cycle. The heating temperature was reduced to 82° C. for the 7th heating cycle.

PAGE 17% 7M urea.

The following table indicates the results.

| Sample | % cross-linked | Total # Counts | Unreacted | Cross-linked | Cycles |
|---|---|---|---|---|---|
| 1 | 1.2 | 11754 | 11607 | 147 | 1 |
| 2 | 6.6 | 7027 | 6563 | 464 | 5 |
| 3 | 2.8 | 8272 | 8037 | 235 | " |
| 4 | 8.0 | 7094 | 6528 | 566 | 10 |
| 5 | 2.9 | 7953 | 7722 | 231 | " |
| 6 | 9.4 | 7280 | 6595 | 685 | 15 |
| 7 | 4.0 | 7020 | 6734 | 286 | " |
| 8 | 23 | 7000 | 5418 | 1582 | " |

Example B

| Component, Nax | pm/λ* | Samples, μl | | | | | | | |
|---|---|---|---|---|---|---|---|---|---|
| | | 1 | 2 | 3 | 4 | 5 | 6 | 7 | 8 |
| ³²P-276 | 0.5 | 2 | 2 | 2 | 2 | 2 | 2 | 2 | 2 |
| 278 | .02 | .8 | .8 | .8 | .8 | .8 | .8 | .8 | .8 |
| 279 | 0.5 | 2.5 | 2.5 | 2.5 | 2.5 | 2.5 | 2.5 | 2.5 | 2.5 |
| H₂O | | 9 | 9 | 9 | 9 | 9 | 9 | 9 | 9 |
| Conditions | | | | | | | | | |
| No. irradiations | | 1 | 2 | 10 | 10 | 10 | 10 | 10 | 10 |
| Heat treatment | | – | Δ | Δ | Δ | Δ | + | + | + |

*pmol/λ;
Δ heat cycle set forth below;
+ isothermal

Protocol

The above procedure was repeated with some modifications. The probe was in 50-fold excess to the target. 75 μl of mineral oil was used. The reactions were run in a a polycarbonate plate. Incubation and heating were on a MJ Research PTC-100 instrument. Irradiation was in a Stratalinker with the heating provided by a mineral oil bath set at 40° C.

Sample 1 was removed after one cycle of irradiation and heating; sample 2 was removed after one cycle of irradiation, heating and an additional irradiation. Samples 3, 4 and 5 received 10 cycles of irradiation of 10 min each, with 9 intervening thermal denaturation cycles in accordance with the following schedule: 84° C. for 3 min; 40° C. for 7 min. Samples 6, 7 and 8 received 10 cycles of irradiation with 9 intervening cycles of remaining in the mineral bath inside the Stratalinker.

The following table indicates the results.

| Sample | % Cross-linked | Total Counts | Unreacted | Cross-linked | Cycles |
|---|---|---|---|---|---|
| 1 | 1.6 | 11641 | 11458 | 183 | 1 |
| 2 | 2.2 | 16744 | 16381 | 363 | 10 |
| 3 | 11.7 | 11190 | 9883 | 1307 | " |
| 4 | 9.5 | 15468 | 13993 | 1475 | " |
| 5 | 8.0 | 17118 | 15759 | 1359 | "* |
| 6 | 2.0 | 15260 | 14954 | 306 | " |
| 7 | 2.2 | 14000 | 13687 | 313 | " |
| 8 | 1.8 | 17925 | 17595 | 330 | " |

*No denaturation

Sample 3 showed approximately 12% cross-linking, while sample 6 showed only about 2% cross-linking, indicating an approximately 6-fold linear amplification.

It is evident from the above results that the subject methodology provides a convenient and efficient way to identify the presence of specific nucleic acid sequences.

Amplification is achieved in the absence of enzyme, using chemical reactions to cross-link two probes tethered together by means of a template. Once the two probes have been cross-linked, they in turn may serve as a template for homologous sequences. In this way, a geometric expansion of cross-linked probes may be obtained in relation to a target sequence.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detecting a target nucleic acid sequence in a sample, said method employing at least one pair of probes characterized by having sequences homologous to adjacent portions of said target nucleic acid sequence and having nucleic acid side chains which non-covalently bind to form a stem upon base pairing of said probes to said target nucleic acid sequence, at least one of said side chains having a photoactivatable group bonded to a difunctional molecule other than a nucleotide in said nucleic acid side chain which photoactivatable group upon photoactivation during stem formation forms a covalent cross-link with the other side chain member of said stem, said method comprising:

combining said sample with said pair of probes under conditions of base pairing between said probes and said target nucleic acid, whereby probes binding to said target nucleic acid form said stem;

photoactivating said photoactivatable group, whereby a covalent cross-link occurs between said side chain members of said stem;

amplifying the amount of cross-linked probes by performing the following steps 1–3 at least once:
   (1) melting double stranded nucleic acid;
   (2) incubating for sufficient time under hybridization conditions for base pairing between homologous sequences to occur; and
   (3) photoactivating said photoactivatable group, whereby a cross-link occurs between said side chain members of said stem; and detecting the presence of cross-linked pairs of probes as indicative of the presence of said target sequence in said sample.

2. A method according to claim 1, wherein said difunctional group is selected from the group consisting of glycerol, dithiothreitol, 1,3,5-trihydroxycyclohexane, and deoxyribose.

3. A method according to claim 1, wherein said amplifying comprises the further step of adding additional said probes to said photoactivating.

4. A method for detecting a target nucleic acid sequence in a sample, said method employing at least one pair of probes characterized by having sequences homologous to adjacent portions of said target nucleic acid sequence and having side chains which non-covalently bind to form a stem upon base pairing of said probes to said target nucleic acid sequence, at least one of said side chains having a photoactivatable group bonded to a difunctional molecule other than a nucleotide in said nucleic acid side chain, which photoactivatable group upon activation during stem formation forms a covalent cross-link with the other side chain member of said stem, each of said side chains having at least two nucleotides capable of base pairing with the other side chain to form said stem, said method comprising:

combining said sample with said pair of probes under conditions of base pairing between said probes and said target nucleic acid, wherein when said target nucleic acid is single stranded, at least a first pair of probes is added which is homologous to said single stranded nucleic acid, and if said target nucleic acid is double stranded, first and second pairs of probes are added, which pairs are homologous to one or the other strands of said double stranded target nucleic acid, whereby probes binding to said target nucleic acid form said stem;

photoactivating said photoactivatable group, whereby a covalent cross-link is formed between said side chain members of said stem;

melting double stranded nucleic acid;

repeating the following cycle at least once:
      incubating for sufficient time for base pairing between homologous sequences to occur, with the proviso that when only said first pair of probes was added, another pair of probes is added having a sequence analogous to said target nucleic acid;
      photoactivating said photoactivatable group, whereby a covalent cross-link is formed between said side chain members of said stem; and
      melting double stranded DNA, which ends a cycle; and detecting the presence of cross-linked pairs of probes as indicative of the presence of said target sequence in said sample.

5. A method according to claim 4, wherein said target sequence has a gap of not more than about 2 nucleotides between the sequences homologous to said pair of probes and each of said side chains of said stem comprise at least three nucleotides which form base pairs.

6. A method according to claim 5, wherein said side chains have from 3 to 8 nucleotides which base pair to form said stem.

7. A method according to claim 4, wherein said photoactivatable group reacts with a nucleotide to form a covalent bond cross-link.

8. A method according to claim 7, wherein said photoactivatable group is a moiety comprising a coumarin or furocoumarin.

9. A method according to claim 4, wherein said detection is by gel electrophoresis.

10. A method according to claim 4, wherein at least three cycles are completed.

11. A method for detecting a sequence of target dsDNA in a sample, said method employing first and second pairs of probes characterized by having sequences homologous to adjacent portions of first and second strands of said target dsDNA and having side chains which non-covalently bind to form a stem upon base pairing of said probes to said target first and second strands, respectively, at least one of said side chains in each pair having a photoactivatable group bonded to a difunctional molecule other than nucleotide in said nucleic acid side chain, which photoactivatable group upon activation during stem formation forms a covalent cross-link with the other side chain member of said stem, each of said side chains having at least two nucleotides capable of base pairing with the other side chain to form said stem, said method comprising:

combining said sample with said first and second pairs of probes under conditions of base pairing between said probes and said target dsDNA, which first and second pairs of probes are homologous to one or the other strands of said target dsDNA, whereby probes binding to said target dsDNA nucleic acid form said stem;

photoactivating said photoactivatable group, whereby a covalent cross-link is formed between said side chain members of said stem;

melting double stranded nucleic acid;

repeating the following cycle at least once:

incubating for sufficient time for base pairing between homologous sequences to occur, with the proviso that when only said first pair of probes was added, another pair of probes is added having a sequence analogous to said target nucleic acid;

photoactivating said photoactivatable group, whereby a covalent cross-link is formed between said side chain members of said stem; and melting double stranded DNA, which ends a cycle; and detecting the presence of cross-linked pairs of probes as indicative of the presence of said target dsDNA in said sample.

12. A method according to claim 11, wherein one of said side chains has a bulge in the side chain between the nucleotide base pairing with said target sequence and directly linked to said side chain and the first nucleotide base pairing with a nucleotide of the other side chain member of said stem.

13. A method according to claim 11, wherein said side chains have from 3 to 8 nucleotides which base pair to form said stem.

14. A method according to claim 11, wherein said photoactivatable group reacts with a nucleotide to form a covalent bond cross-link.

15. A method according to claim 11, wherein said photoactivatable group is a coumarin or furocoumarin.

16. A method according to claim 11, wherein said detection is by gel electrophoresis.

17. A method according to claim 11, wherein at least three cycles are completed.

18. A method for detecting a target nucleic acid sequence in a sample, said method employing at least one pair of probes characterized by having sequences homologous to adjacent portions of said target nucleic acid sequence and having nucleic acid side chains which form from 3 to 16 base pairs upon non-covalently binding to form a stem upon base pairing of said probes to said target nucleic acid sequence, at least one of said side chains having a coumarin or furocoumarin as an activatable group, which upon activation during stem formation forms a covalent cross-link with the other side chain member of said stem, said method comprising:

combining said sample with said pair of probes under conditions of base pairing between said probes and said target nucleic acid, whereby probes binding to said target nucleic acid form said stem;

activating said activatable group, whereby a covalent cross-link occurs between said side chain members of said stem;

melting double stranded nucleic acid:

repeating the following cycle at least once;

incubating for sufficient time for base pairing between homologous sequences to occur with the proviso that when only: said first pair of probes was added, another pair of probes is added having a sequence analogous to said target nucleic acid;

photoactivating said photoactivatable group, whereby a covalent cross-link is formed between said side chain members of said stem; and melting double stranded DNA, which ends a cycle: and detecting the presence of cross-linked pairs of probes as indicative of the presence of said target sequence in said sample.

19. A method according to claim 18, wherein the affinity between probes in solution is less than about $10^{-1}M^{-1}$.

20. A method according to claim 18, wherein said activatable group is a coumarin which covalently bonds with thymidine in the other stem.

21. A method according to claim 18, wherein said stems comprise A and T.

22. A method according to claim 21, wherein the homologous sequence of the probe to the target DNA is in the range of about 25 bases to 0.5 kb.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ATTTTGTCTT TGCGCACAGA CGATCTATTT 30

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AAATAGATCG TCTGTTTGCT TT 22

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 2
        ( D ) OTHER INFORMATION: /N=O-ethyl coumarin"

( x i ) SEQUENCE DESCRIPTION: SEQ ID NO:3:

ANAGCGCGCA AAGACAAAAT    20

(2) INFORMATION FOR SEQ ID NO:4:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:4:

ATTTTGTCTT TGCGCGGCTT T    21

(2) INFORMATION FOR SEQ ID NO:5:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: misc_feature
  (B) LOCATION: 21
  (D) OTHER INFORMATION: /N=O-ethyl coumarin (xi) SEQUENCE DESCRIPTION: SEQ ID NO:5:

AAATAGATCG TCTGTTTGCA NA    22

(2) INFORMATION FOR SEQ ID NO:6:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:6:

TTTGCGCGCA AAGACAAAAT    20

(2) INFORMATION FOR SEQ ID NO:7:

(i) SEQUENCE CHARACTERISTICS:
  (A) LENGTH: 48 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:7:

TTTATAAAAA GCTCGTAATA TGCAAGAGCA TTGTAAGCAG AAGACTTA    48

(2) INFORMATION FOR SEQ ID NO:8:

(i) SEQUENCE CHARACTERISTICS:
  (A) LENGTH: 32 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:8:

TTTATAAAAA GCTCGTAATA TGCTTTTTTT TT                                32

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TAAGTCTTCT GCTTACAATG CTCTTTTTTT TT                                32

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 2
        (D) OTHER INFORMATION: n=O-ethyl coumarin (xi) SEQUENCE DESCRIPTION: SEQ ID NO:10:

ANAAAGCATA TTACGAGCTT TTTATAAA                                     28

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 5
        (D) OTHER INFORMATION:N=O-ethyl coumarin (xi) SEQUENCE DESCRIPTION: SEQ ID NO:11:

AAAANAAGCA TATTACGAGC TTTTTATAAA                                   30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ANAAAAAGCA TATTACGAGC TTTTTATAAA                                   30

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:13:

TAAGTCTTCT GCTTACAATG CTCTTGCATA TTACGAGCTT TTTATAAA    48

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:14:

TAAGTCTTCT GCTTACAATG AACTTGCATA TTACGAGCTT TTTATAAAT    49

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: misc_feature
        (B) LOCATION: 2
        (D) OTHER INFORMATION: N=O-ethyl coumarin (x i) SEQUENCE DESCRIPTION: SEQ ID NO:15:

ANAGCATATT ACGAGCTTTT TATAAA    26

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:16:

TTTTTTTTTC TTGCATATTA CGAGCTTTTT ATAAA    35

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:17:

TTTTTTTTTC ATTGTAAGCA GAAGACTTA    29

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear

```
            ( i i ) MOLECULE TYPE: cDNA ( x i ) SEQUENCE DESCRIPTION: SEQ ID NO:18:

TTTATAAAAA GCTCGTAATA TGCAAGAANA AAA                                           33

( 2 ) INFORMATION FOR SEQ ID NO:19:

( i ) SEQUENCE CHARACTERISTICS:
                    ( A ) LENGTH: 33 base pairs
                    ( B ) TYPE: nucleic acid
                    ( C ) STRANDEDNESS: single
                    ( D ) TOPOLOGY: linear ( i i ) MOLECULE TYPE: cDNA ( x i ) SEQUENCE DESCRIPTION: SEQ ID NO:19:

TTTATAAAAA GCTCGTAATA TGCAAGANAA AAA                                           33
```